(12) United States Patent
Widomski et al.

(10) Patent No.: US 8,753,362 B2
(45) Date of Patent: Jun. 17, 2014

(54) DOUBLE SPIRAL PATENT FORAMEN OVALE CLOSURE CLAMP

(71) Applicant: W. L. Gore & Associates, Flagstaff, AZ (US)

(72) Inventors: David R. Widomski, Wakefield, MA (US); Carol A. Devellian, Topfield, MA (US); Morris Simon, Boston, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 0 days.

(21) Appl. No.: 14/030,964

(22) Filed: Sep. 18, 2013

(65) Prior Publication Data

US 2014/0025095 A1    Jan. 23, 2014

Related U.S. Application Data

(62) Division of application No. 11/008,539, filed on Dec. 9, 2004, now abandoned.

(60) Provisional application No. 60/528,022, filed on Dec. 9, 2003.

(51) Int. Cl.
*A61B 17/08*    (2006.01)

(52) U.S. Cl.
USPC .......................................... 606/151; 606/213

(58) Field of Classification Search
None
See application file for complete search history.

(56) References Cited

U.S. PATENT DOCUMENTS

| | | |
|---|---|---|
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi, Jr. |
| 4,006,747 A | 2/1977 | Kronenthal et al. |
| 4,007,743 A | 2/1977 | Blake |
| 4,149,327 A | 4/1979 | Hammer et al. |

(Continued)

FOREIGN PATENT DOCUMENTS

| | | |
|---|---|---|
| DE | 94 13 645 U1 | 10/1994 |
| EP | 0 362 113 | 4/1990 |

(Continued)

OTHER PUBLICATIONS

Ruddy, A.C. et al., "Rheological, Mechanical and Thermal Behaviour of Radiopaque Filled Polymers", *Polymer Processing Research Centre, School of Chemical Engineering, Queen's University of Belfast*, pp. 167-171, 2004.

(Continued)

*Primary Examiner* — Corrine M McDermott
*Assistant Examiner* — Son Dang
(74) *Attorney, Agent, or Firm* — DLA Piper LLP (US)

(57) ABSTRACT

The present invention provides a device which is adapted to press together the septum primum and the septum secundum between the atrial chambers to close any tunnel in the septum. The device in its preferred form has two clamping members, one on each side of the septum and a central connector which connects the two clamping members and passes through the tunnel. The device is configured to conform to the anatomy such that the tunnel is not substantially deformed by the device. The central connector, in its preferred form has two wires that are spaced apart so that the wires are proximate the lateral sides of the tunnel. The spacing allows the device to be centered at an appropriate location.

9 Claims, 12 Drawing Sheets

(56) References Cited

U.S. PATENT DOCUMENTS

| | | | |
|---|---|---|---|
| 4,425,908 A | 1/1984 | Simon | |
| 4,610,674 A | 9/1986 | Suzuki et al. | |
| 4,626,245 A | 12/1986 | Weinstein | |
| 4,693,249 A | 9/1987 | Schenck et al. | |
| 4,696,300 A | 9/1987 | Anderson | |
| 4,710,181 A | 12/1987 | Fuqua | |
| 4,710,192 A | 12/1987 | Liotta et al. | |
| 4,738,666 A | 4/1988 | Fuqua | |
| 4,836,204 A | 6/1989 | Landymore et al. | |
| 4,840,623 A | 6/1989 | Quackenbush | |
| 4,902,508 A | 2/1990 | Badylak et al. | |
| 4,915,107 A | 4/1990 | Rebuffat et al. | |
| 4,917,089 A | 4/1990 | Sideris | |
| 4,921,479 A | 5/1990 | Grayzel | |
| 4,956,178 A | 9/1990 | Badylak et al. | |
| 5,021,059 A | 6/1991 | Kensey et al. | |
| 5,037,433 A | 8/1991 | Wilk et al. | |
| 5,041,129 A | 8/1991 | Hayhurst et al. | |
| 5,049,131 A | 9/1991 | Deuss | |
| 5,063,640 A | 11/1991 | Link | |
| 5,078,736 A | 1/1992 | Behl | |
| 5,106,913 A | 4/1992 | Yamaguchi et al. | |
| 5,108,420 A | 4/1992 | Marks | |
| 5,149,327 A | 9/1992 | Oshiyama | |
| 5,163,131 A | 11/1992 | Row et al. | |
| 5,167,363 A | 12/1992 | Adkinson et al. | |
| 5,167,637 A | 12/1992 | Okada et al. | |
| 5,171,259 A | 12/1992 | Inoue | |
| 5,176,659 A | 1/1993 | Mancini | |
| 5,192,301 A | 3/1993 | Kamiya et al. | |
| 5,222,974 A | 6/1993 | Kensey et al. | |
| 5,226,879 A | 7/1993 | Ensminger et al. | |
| 5,234,458 A | 8/1993 | Metais | |
| 5,236,440 A | 8/1993 | Hlavacek | |
| 5,245,023 A | 9/1993 | Peoples et al. | |
| 5,245,080 A | 9/1993 | Aubard et al. | |
| 5,250,430 A | 10/1993 | Peoples et al. | |
| 5,257,637 A | 11/1993 | El Gazayerli | |
| 5,275,826 A | 1/1994 | Badylak et al. | |
| 5,282,827 A | 2/1994 | Kensey et al. | |
| 5,284,488 A | 2/1994 | Sideris | |
| 5,304,184 A | 4/1994 | Hathaway et al. | |
| 5,312,341 A | 5/1994 | Turi | |
| 5,312,435 A | 5/1994 | Nash et al. | |
| 5,316,262 A | 5/1994 | Koebler | |
| 5,320,611 A | 6/1994 | Bonutti et al. | |
| 5,334,217 A | 8/1994 | Das | |
| 5,350,363 A | 9/1994 | Goode et al. | |
| 5,350,399 A | 9/1994 | Erlebacher et al. | |
| 5,354,308 A | 10/1994 | Simon et al. | |
| 5,364,356 A | 11/1994 | Hofling | |
| 5,382,259 A * | 1/1995 | Phelps et al. | 606/151 |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,453,099 A | 9/1995 | Lee et al. | |
| 5,478,353 A | 12/1995 | Yoon | |
| 5,480,353 A | 1/1996 | Garza, Jr. | |
| 5,480,424 A | 1/1996 | Cox | |
| 5,486,193 A | 1/1996 | Bourne et al. | |
| 5,507,811 A | 4/1996 | Koike et al. | |
| 5,522,788 A | 6/1996 | Kuzmak | |
| 5,534,432 A | 7/1996 | Peoples et al. | |
| 5,540,712 A | 7/1996 | Kleshinski et al. | |
| 5,562,632 A | 10/1996 | Davila et al. | |
| 5,577,299 A | 11/1996 | Thompson et al. | |
| 5,601,571 A | 2/1997 | Moss | |
| 5,603,703 A | 2/1997 | Elsberry et al. | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | |
| 5,649,950 A | 7/1997 | Bourne et al. | |
| 5,649,959 A | 7/1997 | Hannam et al. | |
| 5,663,063 A | 9/1997 | Peoples et al. | |
| 5,683,411 A | 11/1997 | Kavteladze et al. | |
| 5,690,674 A | 11/1997 | Diaz | |
| 5,693,085 A | 12/1997 | Buirge et al. | |
| 5,702,421 A | 12/1997 | Schneidt | |
| 5,709,707 A | 1/1998 | Lock et al. | |
| 5,713,864 A | 2/1998 | Verkaart | |
| 5,717,259 A | 2/1998 | Schexnayder | |
| 5,720,754 A | 2/1998 | Middleman et al. | |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,772,641 A | 6/1998 | Wilson | |
| 5,776,162 A | 7/1998 | Kleshinski | |
| 5,776,183 A | 7/1998 | Kanesaka et al. | |
| 5,797,960 A | 8/1998 | Stevens et al. | |
| 5,800,516 A | 9/1998 | Fine et al. | |
| 5,810,884 A | 9/1998 | Kim | |
| 5,820,594 A | 10/1998 | Fontirroche et al. | |
| 5,823,956 A | 10/1998 | Roth et al. | |
| 5,829,447 A | 11/1998 | Stevens et al. | |
| 5,853,420 A | 12/1998 | Chevillon et al. | |
| 5,853,422 A | 12/1998 | Huebsch et al. | |
| 5,855,614 A | 1/1999 | Stevens et al. | |
| 5,861,003 A | 1/1999 | Latson et al. | |
| 5,865,791 A | 2/1999 | Whayne et al. | |
| 5,879,366 A | 3/1999 | Shaw et al. | |
| 5,893,856 A | 4/1999 | Jacob et al. | |
| 5,902,287 A | 5/1999 | Martin | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,928,250 A | 7/1999 | Koike et al. | |
| 5,944,691 A | 8/1999 | Querns et al. | |
| 5,944,738 A | 8/1999 | Amplatz et al. | |
| 5,955,110 A | 9/1999 | Patel et al. | |
| 5,976,174 A | 11/1999 | Ruiz | |
| 5,980,505 A | 11/1999 | Wilson | |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,517 A | 1/2000 | Baccaro | |
| 6,019,753 A | 2/2000 | Pagan | |
| 6,024,756 A | 2/2000 | Huebsch et al. | |
| 6,027,509 A | 2/2000 | Schatz et al. | |
| 6,027,519 A | 2/2000 | Stanford | |
| 6,030,007 A | 2/2000 | Bassily et al. | |
| 6,056,760 A | 5/2000 | Koike et al. | |
| 6,071,998 A | 6/2000 | Muller et al. | |
| 6,077,291 A | 6/2000 | Das | |
| 6,077,880 A | 6/2000 | Castillo et al. | |
| 6,079,414 A | 6/2000 | Roth | |
| 6,080,182 A | 6/2000 | Shaw et al. | |
| 6,096,347 A | 8/2000 | Gedees et al. | |
| 6,106,913 A | 8/2000 | Scardino et al. | |
| 6,113,609 A | 9/2000 | Adams | |
| 6,117,159 A | 9/2000 | Buscemi et al. | |
| 6,126,686 A | 10/2000 | Badylak et al. | |
| 6,132,438 A | 10/2000 | Fleischman et al. | |
| 6,143,037 A | 11/2000 | Goldstein et al. | |
| 6,152,144 A | 11/2000 | Van Der Burg et al. | |
| 6,152,935 A * | 11/2000 | Kammerer et al. | 606/144 |
| 6,165,183 A | 12/2000 | Kuehn et al. | |
| 6,165,204 A | 12/2000 | Levinson et al. | |
| 6,168,588 B1 | 1/2001 | Wilson | |
| 6,171,329 B1 | 1/2001 | Shaw et al. | |
| 6,174,322 B1 | 1/2001 | Schneidt | |
| 6,174,330 B1 | 1/2001 | Stinson | |
| 6,183,443 B1 | 2/2001 | Kratoska et al. | |
| 6,187,039 B1 | 2/2001 | Hiles et al. | |
| 6,190,353 B1 | 2/2001 | Garibotto et al. | |
| 6,190,357 B1 | 2/2001 | Ferrari et al. | |
| 6,197,016 B1 | 3/2001 | Fourkas et al. | |
| 6,199,262 B1 | 3/2001 | Martin | |

(56) References Cited

U.S. PATENT DOCUMENTS

| | | |
|---|---|---|
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,443 B1 | 11/2001 | Stone |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,358,238 B1 | 3/2002 | Sherry |
| 6,364,853 B1 | 4/2002 | French et al. |
| 6,371,904 B1 | 4/2002 | Sirimanne et al. |
| 6,375,625 B1 | 4/2002 | French et al. |
| 6,375,671 B1 | 4/2002 | Kobayashi et al. |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Van Der Burg et al. |
| 6,426,145 B1 | 7/2002 | Moroni |
| 6,432,134 B1 * | 8/2002 | Anson et al. ............... 623/1.19 |
| 6,436,088 B2 | 8/2002 | Frazier et al. |
| 6,440,152 B1 | 8/2002 | Gainor et al. |
| 6,450,987 B1 | 9/2002 | Kramer |
| 6,460,749 B1 | 10/2002 | Levinson et al. |
| 6,482,224 B1 | 11/2002 | Michler et al. |
| 6,488,706 B1 | 12/2002 | Solymar |
| 6,494,846 B1 | 12/2002 | Margolis |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,554,842 B2 | 4/2003 | Heuser et al. |
| 6,585,719 B2 | 7/2003 | Wang |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,506 B2 | 9/2003 | McGuckin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,656,206 B2 | 12/2003 | Corcoran et al. |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,790,173 B2 | 9/2004 | Saadat et al. |
| 6,828,357 B1 | 12/2004 | Martin et al. |
| 6,838,493 B2 | 1/2005 | Williams et al. |
| 6,867,248 B1 | 3/2005 | Martin et al. |
| 6,867,249 B2 | 3/2005 | Lee et al. |
| 6,921,410 B2 | 7/2005 | Porter |
| 6,936,058 B2 | 8/2005 | Forde et al. |
| 6,949,116 B2 | 9/2005 | Solymar et al. |
| 7,022,102 B2 | 4/2006 | Paskar |
| 7,097,653 B2 | 8/2006 | Freudenthal et al. |
| 7,186,251 B2 | 3/2007 | Malecki et al. |
| 7,192,435 B2 | 3/2007 | Corcoran et al. |
| 7,288,105 B2 | 10/2007 | Oman et al. |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor |
| 2003/0004533 A1 | 1/2003 | Deck et al. |
| 2003/0023266 A1 | 1/2003 | Welch et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbas et al. |
| 2003/0100920 A1 | 5/2003 | Akin et al. |
| 2003/0120337 A1 | 6/2003 | Van Tassel et al. |
| 2003/0139819 A1 | 7/2003 | Beer et al. |
| 2003/0171774 A1 | 9/2003 | Seigner et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2003/0225421 A1 | 12/2003 | Peavey et al. |

(56) References Cited

U.S. PATENT DOCUMENTS

| | | | |
|---|---|---|---|
| 2004/0044361 A1 | 3/2004 | Frazier et al. | |
| 2004/0073242 A1 | 4/2004 | Chanduszko | |
| 2004/0087968 A1 | 5/2004 | Core | |
| 2004/0158124 A1 | 8/2004 | Okada | |
| 2004/0176799 A1 | 9/2004 | Chanduszko et al. | |
| 2004/0210301 A1 | 10/2004 | Obermiller | |
| 2004/0234567 A1 | 11/2004 | Dawson | |
| 2004/0249367 A1 | 12/2004 | Saadat et al. | |
| 2005/0025809 A1 | 2/2005 | Hasirci et al. | |
| 2005/0043759 A1 | 2/2005 | Chanduszko | |
| 2005/0080430 A1 | 4/2005 | Wright et al. | |
| 2005/0113868 A1 | 5/2005 | Devellian et al. | |
| 2005/0131341 A1 | 6/2005 | McGuckin et al. | |
| 2005/0251154 A1* | 11/2005 | Chanduszko et al. | 606/151 |
| 2005/0267523 A1 | 12/2005 | Devellian et al. | |
| 2005/0273135 A1 | 12/2005 | Chanduszko et al. | |
| 2005/0288786 A1 | 12/2005 | Chanduszko | |
| 2006/0052821 A1* | 3/2006 | Abbott et al. | 606/213 |
| 2006/0122647 A1 | 6/2006 | Callaghan et al. | |
| 2006/0265004 A1 | 11/2006 | Callaghan et al. | |
| 2006/0271089 A1 | 11/2006 | Alejandro et al. | |
| 2007/0010851 A1 | 1/2007 | Chanduszko et al. | |
| 2007/0073337 A1* | 3/2007 | Abbott et al. | 606/213 |
| 2007/0167981 A1 | 7/2007 | Opolski | |

FOREIGN PATENT DOCUMENTS

| | | |
|---|---|---|
| EP | 0 474 887 | 3/1992 |
| EP | 0 839 549 A | 5/1998 |
| EP | 0 861 632 | 9/1998 |
| EP | 1 013 227 A2 | 6/2000 |
| EP | 1 046 375 | 10/2000 |
| EP | 1 222 897 | 7/2002 |
| WO | WO-96/25179 | 8/1996 |
| WO | WO-96/31157 | 10/1996 |
| WO | WO-98/07375 A1 | 2/1998 |
| WO | WO-98/08462 | 3/1998 |
| WO | WO-98/16174 | 4/1998 |
| WO | WO-98/29026 A | 7/1998 |
| WO | WO-98/51812 | 11/1998 |
| WO | WO-99/05977 A1 | 2/1999 |
| WO | WO-98/18864 | 4/1999 |
| WO | WO-99/18862 A1 | 4/1999 |
| WO | WO-99/18864 A1 | 4/1999 |
| WO | WO-99/18870-AI | 4/1999 |
| WO | WO-99/18871 A1 | 4/1999 |
| WO | WO-99/30640 | 6/1999 |
| WO | WO-99/66846 | 12/1999 |
| WO | WO-00/27292 | 5/2000 |
| WO | WO-00/44428 | 8/2000 |
| WO | WO-01/08600 | 2/2001 |
| WO | WO-01/19256 | 3/2001 |
| WO | WO-01/21247 A1 | 3/2001 |
| WO | WO-01/28432 | 4/2001 |
| WO | WO-01/30268 A1 | 5/2001 |
| WO | WO-01/49185 | 7/2001 |
| WO | W0-01/78596 A | 10/2001 |
| WO | WO-01/93783 | 12/2001 |
| WO | WO-02/17809 M | 3/2002 |
| WO | WO-02/24106 | 3/2002 |
| WO | WO-02/0198563 | 12/2002 |
| WO | WO-03/001893 | 1/2003 |
| WO | WO-03/024337 | 3/2003 |
| WO | WO-03/053493 A | 7/2003 |
| WO | WO-03/059152 | 7/2003 |
| WO | WO-03/063732 A | 8/2003 |
| WO | WO-03/077733 | 9/2003 |
| WO | WO-03/082076 | 10/2003 |
| WO | WO-03/103476 A | 12/2003 |
| WO | WO-2004/032993 | 4/2004 |
| WO | WO-2004/037333 | 5/2004 |
| WO | WO-2004/043266 | 5/2004 |
| WO | WO-2004/043508 | 5/2004 |
| WO | WO-2004/052213 | 6/2004 |
| WO | WO-2004/0210301 | 10/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

International Search Report, International Application No. PCT/US03/17390, mailed Oct. 6, 2003 (4 pgs).

Kimura, A., et al., "Effects of Neutron Irradiation on the Transformation Behavior in Ti-Ni Alloys," Abstract, Proceedings of the Intl Conf. on Mariensitic Transformations, 1992, pp. 935-940.

Meier, MD, Bernhard et al., "Contemporary Management of Patent Foramen Ovale," American Heart Association, Inc., Circulation, 2003, vol. 107, pp. 5-9.

Nat'l Aeronautics and Space Administration, "55-Nitinol—The Alloy with a Memory: Its Physical Metallurgy, Properties and Applications," NASA Report, pp. 24-25.

Ramanathan, G., et al., "Experimental and Computational Methods for Shape Memory Alloys," 15th ASCE Engineering Mechanics Conference, Jun. 2-5, 2002.

Ruiz, et al, "The Puncture Technique: A New Method for Transcatheter Closure of Patent Foramen Ovale," Catheterization and Cardiovascular Interventions, 2001, vol. 53, pp. 369-372.

Shabalovskaya, S., "Surface, Corrosion and Biocompatibility Aspects of Nitinol as an Ir,nplant Material," Bio-Medical Materials and Engineering, 2002, vol. 12, pp. 69-109.

SMST-2000, "Proceedings of the International Conference on Shape Memory and Superelastic Technologies," Apr. 30 to May 4, 2000, Asilomar Conference Center.

Stockel, "Nitinol Medical Devices and Implants," SMST-2000 Conference Proceedings, 2001, pp. 531-541.

Uchil, J , "Shape Memory Alloys—Characterization Techniques," Pramana—Journal of Physics, 2002, vol. 58(5)(6), pp. 1131-1139.

Athanasiou, T., "Coronary Artery Bypass with the Use of a Magnetic Distal Anastomotic Device: Surgical Technique and Preliminary Experience," The Heart Surgery Forum #20041024, 2004, 4 pgs.

Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.

European Examination Report, European Application No. 03729663.9, mailed Jul. 16, 2008 (5 Pages).

European Examination Report, European Application No. 03731562.9, mailed Jul. 18, 2008 (3 Pages).

European Examination Report, European Application No. 03779297.5, mailed Mar. 15, 2007 (6 Pages).

European Examination Report, European Application No. 04781644.2, mailed Aug. 23, 2007 (3 Pages).

Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.

Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.

\* cited by examiner

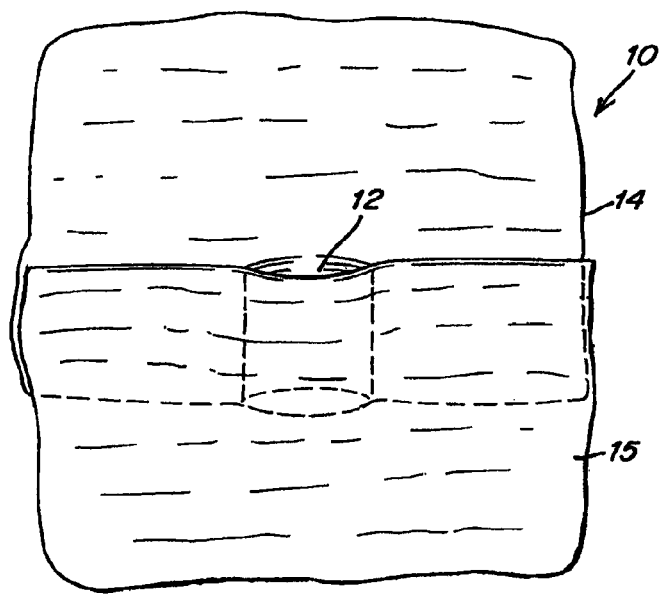
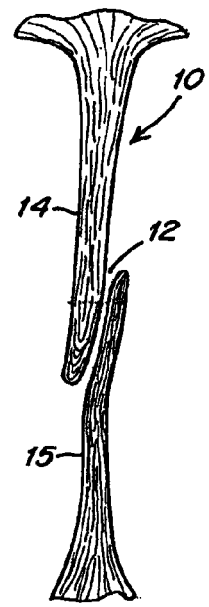
Fig. 1   Fig. 2
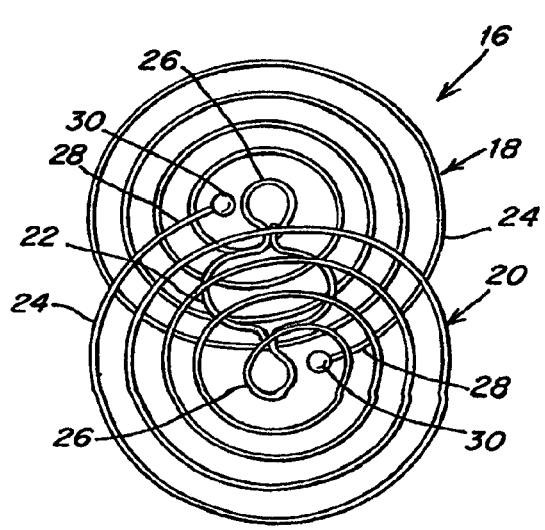
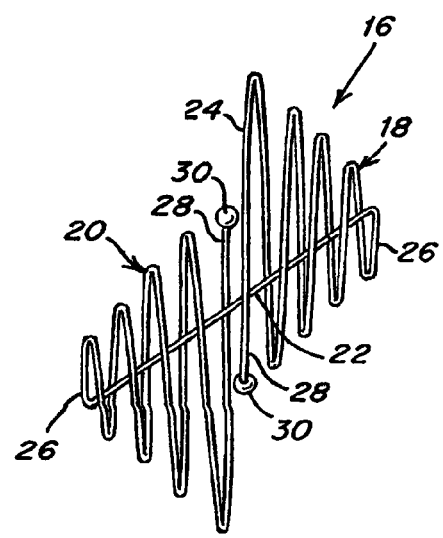
Fig. 3   Fig. 4

DOUBLE SPIRAL PATENT FORAMEN OVALE CLOSURE CLAMP

CROSS-REFERENCE TO RELATED APPLICATION

This application is a divisional application of U.S. application Ser. No. 11/008,539 filed Dec. 4, 2004, now abandoned; and claims priority to provisional patent application 60/528,022 filed Dec. 9, 2003, which is incorporated by reference herein.

BACKGROUND OF THE INVENTION

1. Field of the Invention

The present invention relates to devices and methods which are used to close septal openings. In particular, this invention is directed to devices and methods which are used to close a patent foramen ovale (PFO) in the septum between the left atrium and right atrium.

2. Background Information

A PFO, illustrated in FIGS. 1 and 2, is a persistent, one-way, usually flap-like opening in the wall between the right atrium and left atrium of the heart. Because left atrial (LA) pressure is normally higher than right atrial (RA) pressure, the flap usually stays closed. Under certain conditions, however, right atrial pressure can exceed left atrial pressure which creates the possibility that blood could pass from the right atrium to the left atrium and allow blood clots to enter the systemic circulation. It is desirable that this circumstance be reduced.

The foramen ovale serves a desired purpose when a fetus is gestating in utero. Since blood is oxygenated through the umbilical chord, and not through the developing lungs, the circulatory system of a heart in a fetus allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue the septum secundum 14 and septum primum 15. However, a PFO has been shown to persist in a number of adults.

The presence of a PFO is generally considered to have no therapeutic consequence in otherwise healthy adults. However, patients suffering a stroke or transient ischemic attack (TIA) in the presence of a PFO and without another cause of ischemic stroke paradoxical embolism via a PFO is considered in the diagnosis. While there is currently no proof for a cause-effect relationship, many studies have confirmed a strong association between the presence of a PFO and the risk for paradoxical embolism or stroke. In addition, there is good evidence that patients with PFO and paradoxical embolism are at increased risk for future, recurrent cerebrovascular events.

Accordingly, patients with an increased future risk are considered for prophylactic medical therapy to reduce the risk of a recurrent embolic event. These patients are commonly treated with oral anticoagulants, which have the potential for adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close the PFO. The surgery would typically include suturing a PFO closed by attaching the septum secundum to the septum primum. This sutured attachment can be accomplished with either an interrupted or a continuous stitch and is a common way a surgeon shuts a PFO under direct visualization.

Umbrella devices and a variety of other similar mechanical closure designs, developed initially for percutaneous closure of atrial septal defects (ASDs), have been used in some instances to close PFOs. These devices have the potential to allow patients to avoid the potential side effects often associated with anticoagulation therapies and the risks of invasive surgery. However, umbrella devices and the like which are designed for ASDs are not optimally suited for use as a PFO closure device.

Currently available designs of septal closure devices present drawbacks, including that the implantation procedure is technically complex. Additionally, there are not insignificant complication rates due to thrombus, fractures of the components, conduction system disturbances, perforations of heart tissue, and residual leaks. Many devices have high septal profile and may include large masses of foreign material which may lead to unfavorable body adaptation of a device. Since ASD devices are designed to occlude a hole, many lack anatomic conformability to the PFO flap-like anatomy. That is, when inserting an ASD into the heart to close a PFO, the narrow opening and the thin flap may form impediments to proper deployment. Even if an occlusive seal is formed, the device may be deployed in the heart on an angle which could leave some components not securely seated against the septum. Finally, some septal closure devices are complex to manufacture, which may result in lack of consistency in product performance.

Nitinol (an alloy of nickel and titanium) is known to be used in medical devices because of its biocompatablity and, especially, its unique properties. Nitinol is a member of a class of materials which exhibit shape memory characteristics. Specifically, nitinol has the ability to "remember" a shape and, after being deformed, will return to that shape once a certain temperature is reached. Hence, nitinol has been used to create medical devices that have a desired configuration in the body, e.g., a vena cava filter. The device is deformed into a delivery configuration (generally a reduced profile for delivery through a catheter). Once the device is delivered to the desired site, the nitinol changes configuration into the desired shape upon achieving a certain temperature. This is generally considered thermal responsive shape memory. Nitinol, and other materials, also exhibit superelastic shape memory. In this case, the nitinol can be restrained in a delivery configuration and then will return to the desired configuration as the device leaves the delivery catheter. Of course, some devices can be a combination of thermally induced shape memory and superelastic shape memory.

The present invention is designed to address these and other deficiencies of the prior art septal closure devices.

SUMMARY OF THE INVENTION

The present invention provides a device which is adapted to press together the septum primum and the septum secundum between the atrial chambers to close any tunnel in the septum. The device in its preferred form has two clamping members, one on each side of the septum and a central connector which connects the two clamping members and passes through the tunnel. The device is configured to conform to the anatomy such that the tunnel is not substantially deformed by the device. The central connector, in its preferred form has two wires that are spaced apart so that the wires are proximate the lateral sides of the tunnel. The spacing allows the device to be centered at an appropriate location.

In a preferred form of the device, the clamping members are spirals which are formed from nitinol. The spirals may be constructed of wire, or alternatively, may be constructed of nitinol sheets which have been cut or shaped to form the spirals. The spirals may circle around more or less than 360 degrees and may have the a helical form. In one preferred embodiment the connector may be attached to the inner end of the wire that forms the spiral, in another, the connector may be attached to the outer end of the wire that forms the spiral. Of course, depending on the desired configuration, the connector may be connected to the inner location on one side of the device and the outer location on the other side of the device.

The clamping member may be a spiral or some other structure or configuration which secures the septum together. For example, a plurality of wires may be used which could be spread out along the septum to provide the desired clamping force. Other shapes and orientations could be used which would spread the clamping force over a sufficient surface area to accomplish the desired effect.

The connecting member may be two or more wires which are configured to spread apart in the PFO tunnel. The spacing of the wires is sized to center the device in the desired clamping location in the septum. In one preferred embodiment, the wires are joined at ends and bow apart from each other to fit within the PFO tunnel. Alternatively, the wires may form an S-shaped curve to improve the centering location. Other shapes and configurations are possible.

In an alternate form the connecting member may be formed of thin wires that are wound into a helix (e.g., in the shape of a coil spring). The connecting member may have one or more helically wound wires that form the connecting member. The resultant connector may be shaped in the same manner as the other embodiments. In other embodiments, the connecting member may have an abrasive surface so that a healing response may be stimulated by the abrasive surface. Additionally, the abrasive surface may be directionally oriented. That is, if one were to feel the surface of the wire in one direction, the wire would feel smooth and in the other direction, the wire would feel abrasive or rough.

In still other embodiments, the connecting member may include a film which extends between the connecting wires. The film may be comprised of and/or impregnated with biological and/or bioresorbable material. In another embodiment a joint may be formed at a location along the length of the connecting member. The joint reduces the trauma of the closure device within the PFO. The device may also have a hook or some other piercing element to maintain the PFO closure device in the desired location. Of course, each of the configurations could be used in combination.

The device, in its preferred form, is adapted to be delivered through a catheter into the atria. The device is constrained into a delivery profile and introduced into a catheter for delivery to the heart. Once the catheter is located at the desired delivery site, the device is deployed into the site and changes shape into the desired configuration. The shape change could be a result of a thermally induced shape change or a change due to the superelastic character of the material. Once in the delivery location, the catheter is withdrawn.

BRIEF DESCRIPTION OF THE DRAWINGS

FIG. 1 is a front elevational view from the left atrium of the atrial septum with patent foramen ovale (PFO);

FIG. 2 is a cross-sectional view of the atrial septum of FIG. 1;

FIG. 3 is a bottom plan view of the double spiral patent foramen ovale closure clamp of the present invention showing the connecting central loop;

FIG. 4 is a view in side elevation of the double spiral PFO closure clamp of FIG. 3;

DESCRIPTION OF THE PREFERRED EMBODIMENTS

Figures 5A, 5B, 5C:
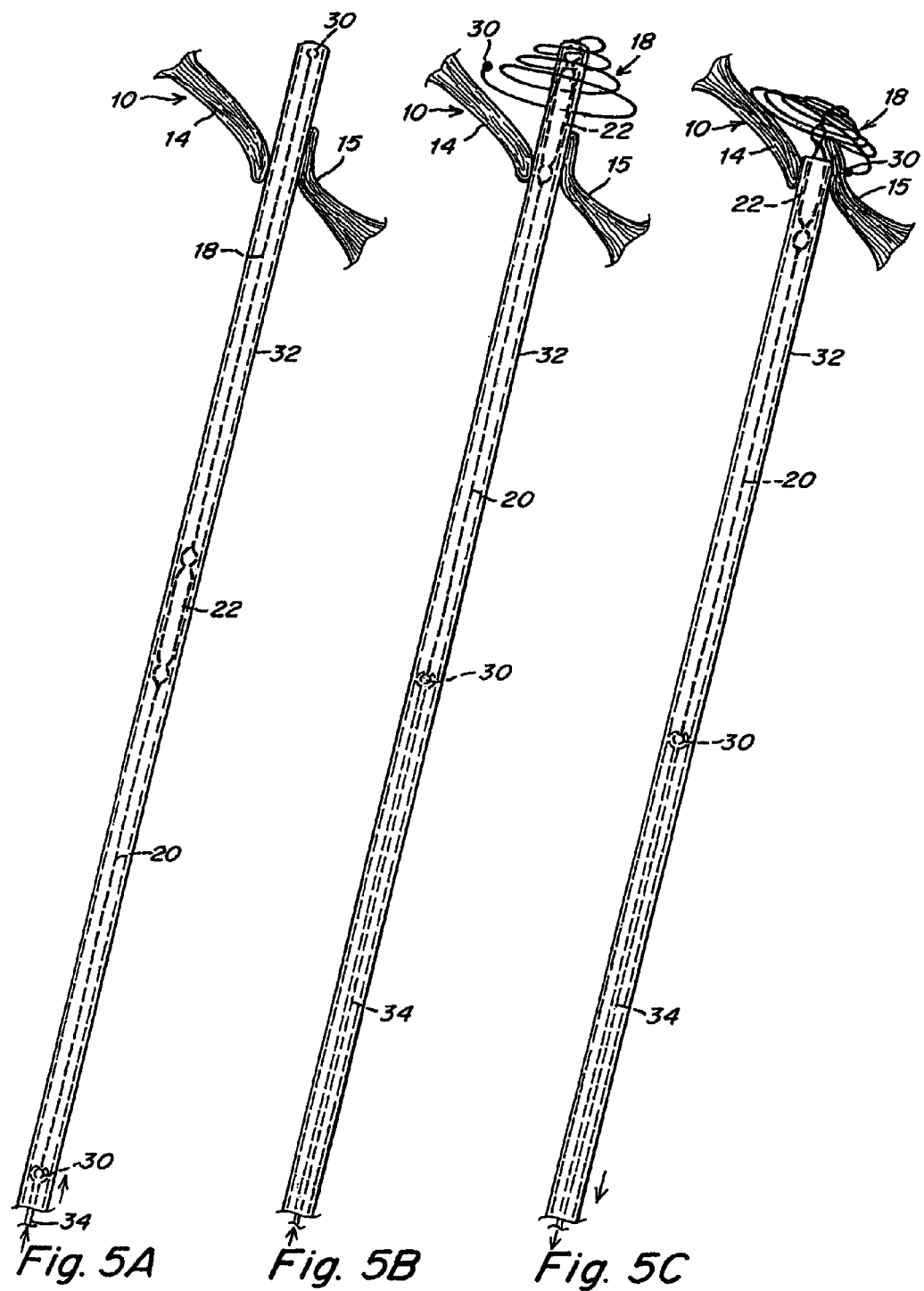
FIG. 5 A-5G show the steps for inserting the double spiral PFO closure clamp of FIGS. 3 and 4.

With reference to FIGS. 1 and 2, the atrial septum 10 divides the left atrium and right atrium of the heart. The patent foramen ovale (PFO) channel 12 extends between the left and right atria and is closed by a flap 14 and 15. Due to the overlap of the septum primum over the septum secundum, the PFO channel or tunnel extends substantially parallel to the surface of the atrial septum. The anatomical structure presents a problem when attempts are made to use conventional septal occluders with opposed, spaced, parallel sections (possibly spiral) are joined by a straight wire or bridge which is substantially perpendicular to the planes of engagement between the sections and the atrial septum. The straight wire or bridge deforms the channel 12 and often prevents proper closure even when the septum primum and the septum secundum are biased toward one another by the spiral sections of the occluder.

Referring to FIGS. 3-7, the double spiral PFO closure clamp of the present invention indicated generally at 16 includes a left atrial spiral section 18 and an opposed right atrial spiral section 20 which are joined by an inclined central loop 22. The loops of each spiral extend progressively outward from the base loop in different planes, and the innermost loops 26 of the two spiral sections 18 and 20 are connected by the inclined central loop 22. The outermost free ends 28 of the base loops 24 are provided with protective balls 30.

With continued reference to FIGS. 3-7, in a preferred embodiment, the spirals that are disposed on each side of the septum and press against the septum with sufficient force to stabilize the device in the desired location. As illustrated, inner loops are connected and the outer loops are configured to compress against the septum. In an alternative configuration, not illustrated, the outer loops may be connected and the inner loops may be configured to press against the septum. In each embodiment, the center joint is configured to connect the loops and, according to several embodiments, the center joint is configured to center the device in the desired delivery location because the center joint is configured to spread out within the PFO tunnel and, as a result, become centered within the PFO tunnel.

The ball 30 of the right atrial spiral section 20 may be grasped and drawn into a protective sheath. As the free end 28 of the right atrial spiral section is drawn inwardly into the protective sheath, the coils of the spiral section straighten as they are drawn into the sheath until the inclined central loop 22 is reached. Then as the central loop enters the sheath, the sides of the central loop are compressed together, and as the central loop is enclosed by the sheath and moves inwardly, it draws the loops of the left atrial spiral section 18, beginning with the innermost loop 26, as a straight section into the sheath.

FIG. 5A shows the double spiral PFO closure clamp in straightened form enclosed by sheath 32. The tip of the sheath may be curved to assist the recovery of the curved loops of the double spiral PFO closure clamp. Here, the sheath is inserted through the PFO channel 12 from the right atrium into the left atrium, and the left atrium, and in FIG. 5B, a wire 34 connected within the sheath to the free end 28 of spiral section 20 forces the spiral section 18 out of the sheath so that it is deployed in the left atrium. Subsequently, as shown in FIG. 5C, the sheath and wire 34 are withdrawn toward the right atrium to draw the spiral section 18 against the atrial septum 10.

Figures 5D, 5E, 5F, 5G:
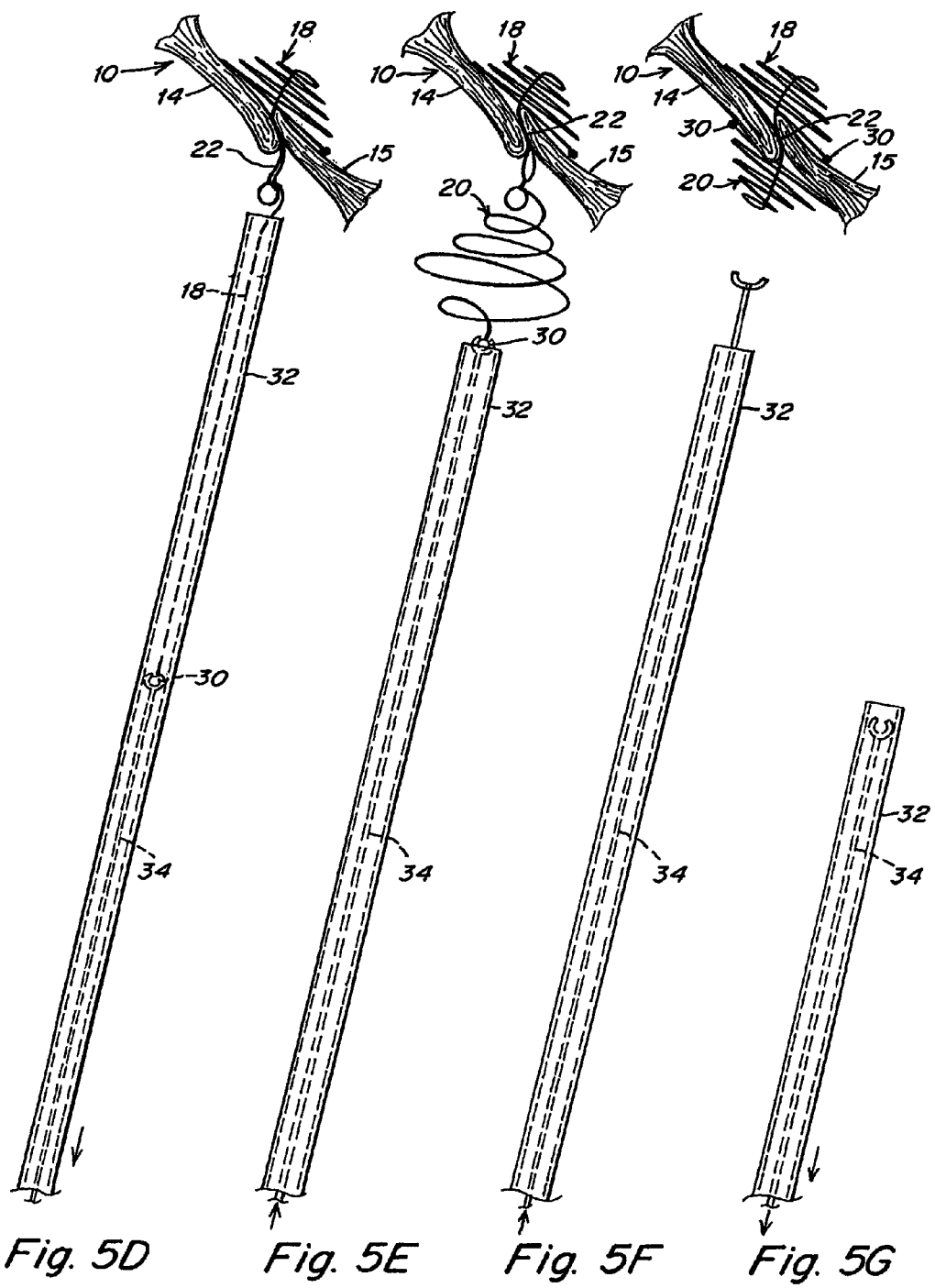

In FIG. 5D, after the inclined central loop 22 has been positioned within the sheath 32 in the PFO channel 12, the sheath is withdrawn to deploy and seat the inclined central loop in the PFO channel. Then, as shown in FIG. 5E, the wire 34 ejects the spiral section 20 into the right atrium against the atrial septum. In FIG. 5F, the wire 34 is released from the free end of the spiral section 20, and in FIG. 5G, the sheath 32 and wire 34 are withdrawn.

The spiral sections 18 and 20 are formed to be urged toward one another. Also, since the loops of each opposed spiral section 18 and 20 are in different planes and since the inclined central loop 22 joins the innermost loops 26 of each spiral section, the spiral section 18 will draw the spiral section 20 against the atrial septum once it is deployed from sheath 32.

Figure 6:
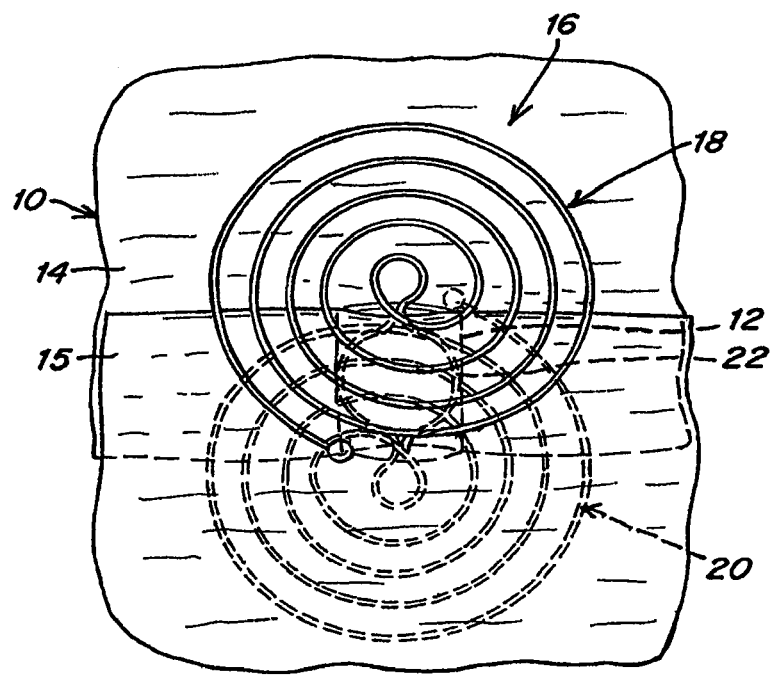
FIG. 6 is a front elevational view from the left atrium of the double spiral PFO closure clamp in place with the central loop in the PFO channel.
Figure 7:
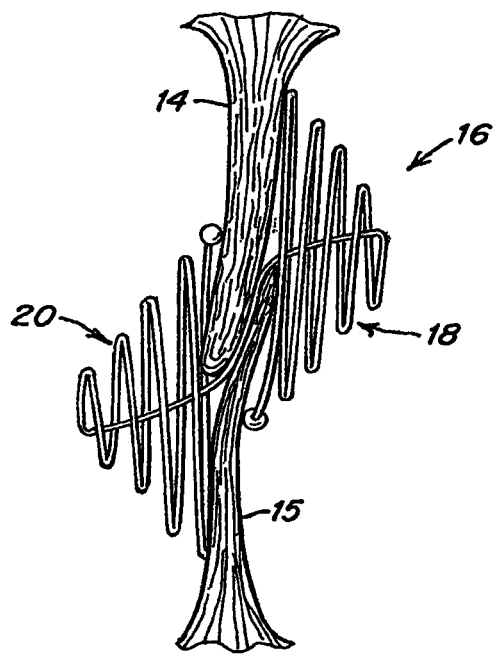
FIG. 7 is a cross-sectional view of the atrial septum and double spiral PFO closure clamp of FIG. 5.

FIGS. 6 and 7 show the double spiral PFO closure clamp 16 in place with the inclined central loop 22 seated in the PFO channel. The spiral sections 18 and 20 are not aligned but are offset so that the inclined central loop follows the PFO channel and does not deform the channel 12. However, enough of the two spiral sections overlap so that the septum primum and the septum secundum are engaged thereby and biased to a closed position.

Since the inclined central loop 22 which joins the spiral sections 18 and 20 is seated in the PFO channel, it prevents shift or rotation of the spiral sections which might occur if a straight non-looped joined piece was used between the spiral sections.

Figure 8:
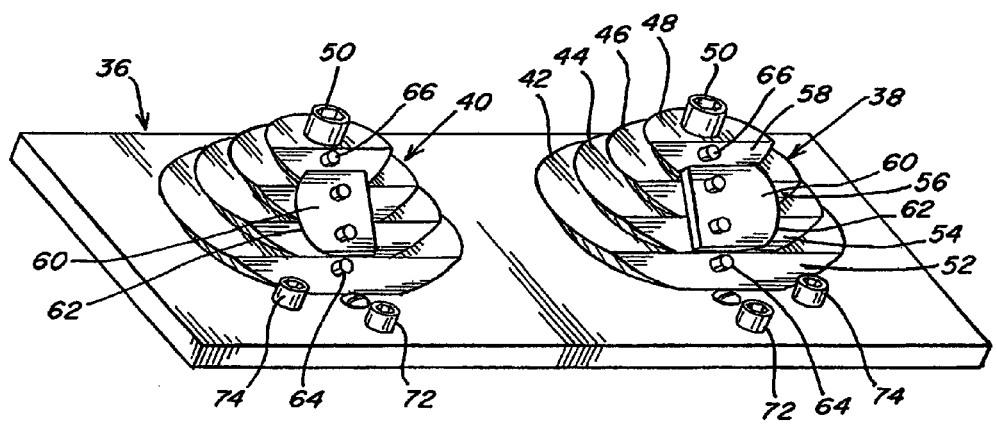
FIG. 8 is a perspective view of a jig for forming the double spiral PFO closure clamp of the present invention.
Figure 9:
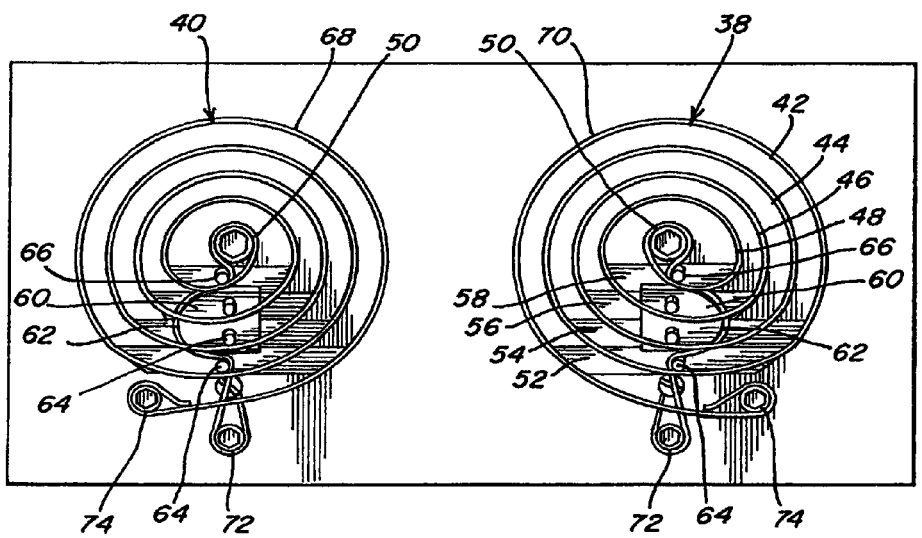
FIG. 9 is a top plan view of the jig of FIG. 7 with spiral sections of the double spiral PFO closure clamp of the present invention wound thereon.

FIGS. 8 and 9 disclose a jig 36 used to manufacture the double spiral PFO closure clamp 16. The jig includes two stepped cone shaped sections 38 and 40 which are each used to form one of the spiral sections 18 or 20 and one half of the inclined central loop 22. Each stepped cone shaped section includes a plurality of arcuate sections 42, 44, 46, and 48 of progressively decreasing size which terminate at a small, circular projection 50. The front faces 52, 54, 56, and 58 of each of the arcuate sections is flat and supports an inclined mandrel 60 having an arcuate side 62. The arcuate side 62 faces left on the cone shaped section 38 and right on the cone shaped section 40. The front faces 52 and 58 support projecting pins 64 and 66 respectively positioned above and below the arcuate side of the mandrel 60.

To form the double spiral PFO closure clamp 16, an elongate length of wire is formed upon each of the cone shaped sections 38 and 40 as shown in FIG. 9. Each of these lengths of wire 68 and 70 are preferably formed of shape memory material such as nitinol and are annealed after being wound in place on the stepped, cone shaped sections 38 and 40. The wire is wound clockwise on the cone shaped section 38 and counter-clockwise on the cone shaped section 40. Each length of wire begins at starting pin 72 and extends around the projecting pin 64 and the arcuate side 62 to the projecting pin 66. The wire extends behind the projecting pin 66 and around the circular projection 50. At the flat face 58, the wire drops and extends around the arcuate section 48 to the flat face 56 where the wire drops again to extend around the arcuate section 44, and at the flat face 52, the wire drops to extend around the arcuate section 42 to a terminal post 74. Thus the two spiral sections 18 and 20 of FIG. 4 are formed. Once the two wire sections are processed on the jig 36, they are removed from the core shaped sections 38 and 40 and one is inverted and rotated relative to the other so that the inclined, arcuate wire sections formed on the mandrels 60 may be welded together to form the inclined central loop 22. Now the free ends of each wire section which were held by the terminal pins 74 are provided with the protective balls 30.

Figure 10:
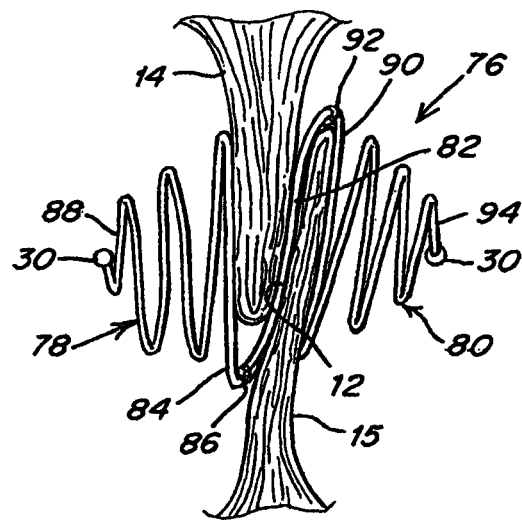
FIG. 10 is a view in side elevation of a second embodiment of the double spiral PFO closure clamp of the present invention.
Figure 11:
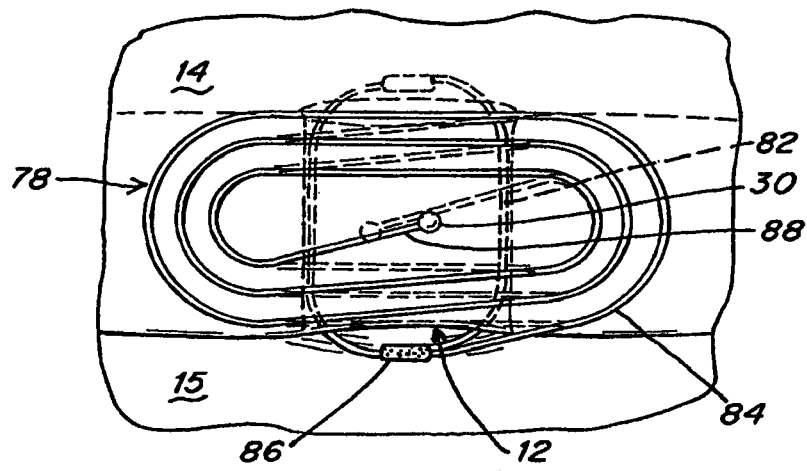
FIG. 11 is a front elevational view from the right atrium of the double spiral PFO closure clamp of FIG. 10.
Figure 12:
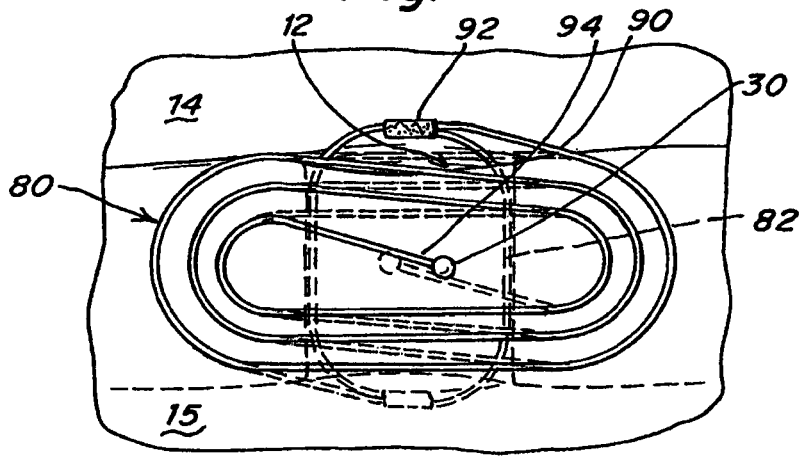
FIG. 12 is a front elevational view from the left atrium of the double spiral PFO closure clamp of FIG. 10.

With reference to FIGS. 10-12, a second embodiment of the double spiral PFO closure clamp of the present invention is indicated generally at 76. The double spiral PFO closure clamp 76 includes a right atrial spiral section 78 to contact the right side of the septum and an opposed left atrial spiral section 80 to contact the left side of the septum. These two spiral sections are joined by an inclined central loop 82 which rests in the PFO channel 12. Unlike the offset atrial spiral sections 18 and 20 of the PFO closure clamp 16, the atrial spiral sections 78 and 80 of the PFO closure clamp 76 are directly opposed in substantial alignment when they are deployed against the atrial septum. This is facilitated by connecting the large, outermost loop of each atrial spiral section to the inclined central loop 82.

As shown by FIG. 11, the outermost loop 84 of the right atrial spiral section 78 is connected to the bottom of the central loop 82 at 86, and curves upwardly over the septum and then inwardly to form the smaller inner loops of the right atrial spiral section. These inner loops terminate at an innermost free end 88 provided with a protective ball 30.

To form the left atrial spiral section 80 in opposed alignment with the right atrial spiral section, the outermost loop 90 is connected to the top of the central loop 82 at 92 as shown by FIG. 12. The outermost loop 90 then curves downwardly over the septum and then inwardly to form the inner loops of the left atrial spiral section. These inner loops terminate at an innermost free end 94 provided with a protective ball 30.

The outermost loops 84 and 90 are configured to position the left atrial spiral section and right atrial spiral section in aligned, opposed relationship.

Figure 13:
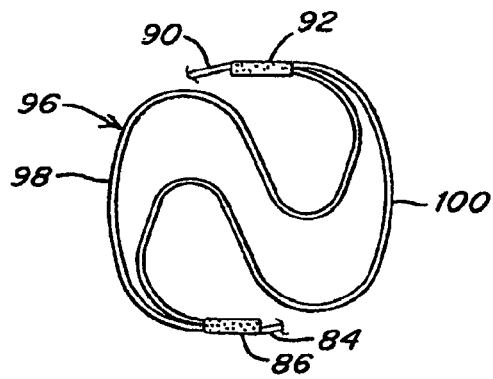
FIG. 13 is a view in front elevation of a second embodiment of a central connector for a PFO closure clamp of FIG. 10.
Figure 14A:
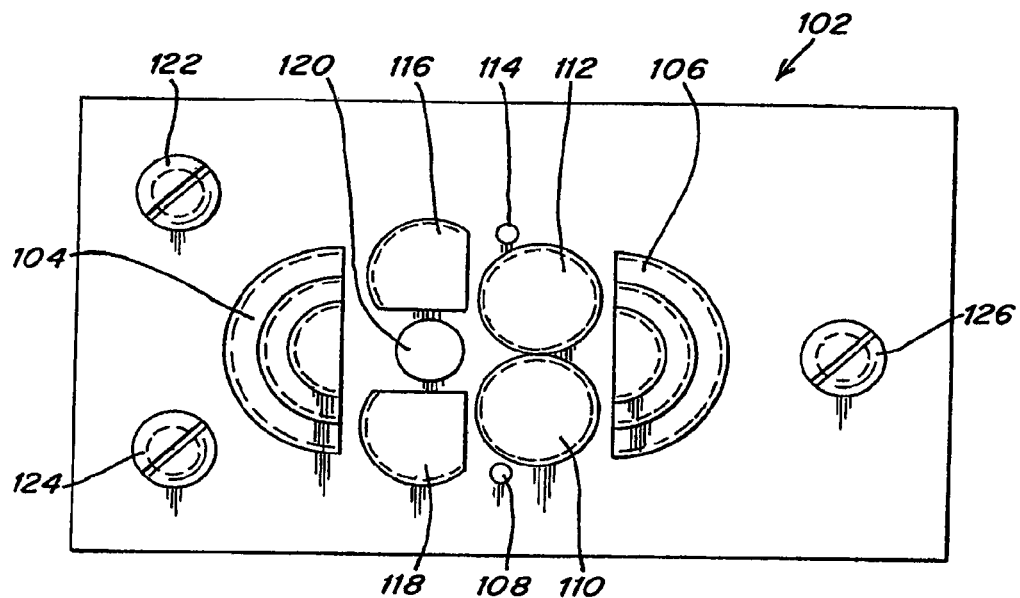
FIGS. 14A and 14B are a plan view and a view in side elevation, respectively of a jig for forming the double spiral PFO closure clamp of FIG. 10 with the central connector of FIG. 13.
Figure 14B:
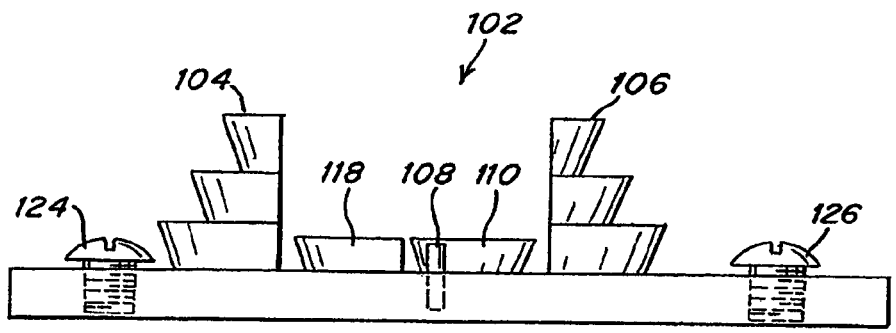

Instead of connecting the two spiral sections 78 and 80 with a central loop which rests in the PFO channel, the central loop can be replaced with the double "S" shaped connector 96 of FIG. 13. This connector has rounded side surfaces 98 and 100 which engage the sides of the PFO channel, but the connections 86 and 92 with the outer loops 84 and 90 of the spiral sections 78 and 80 are oriented in opposite directions by the configuration of the connector. Thus forces on the connector from the spirals which would tend to cause shifting of a round central loop are offset to oppose shifting of the connector.

FIGS. 14A and 14B, 15A and 15B, 16A and 15B, and 17A and 17B show the manner in which the double spiral PFO closure clamp 76 with the double "S" shaped connector 96 is formed. A split jig 102 is used to form both the right atrial spiral section 78 and the left atrial spiral section 80. The jig includes two spaced stepped sections 104 and 106 having opposed arcuate steps which progressively decrease in size. Between the stepped sections are formed to form the double "S" shaped connector 96. These forms include a pin 108 which projects adjacent to a round form 110. This round form 110 contacts a second round form 112 which is adjacent to a second projection pin 114. Spaced from but adjacent to the round forms 110 and 112 are two spaced arcuate forms 116 and 118. Centered between the arcuate forms 116 and 118 is a round form 120. Wire end retaining screws 122, 124, and 126 are positioned outwardly from the stepped sections 104 and 106.

Figure 15A:
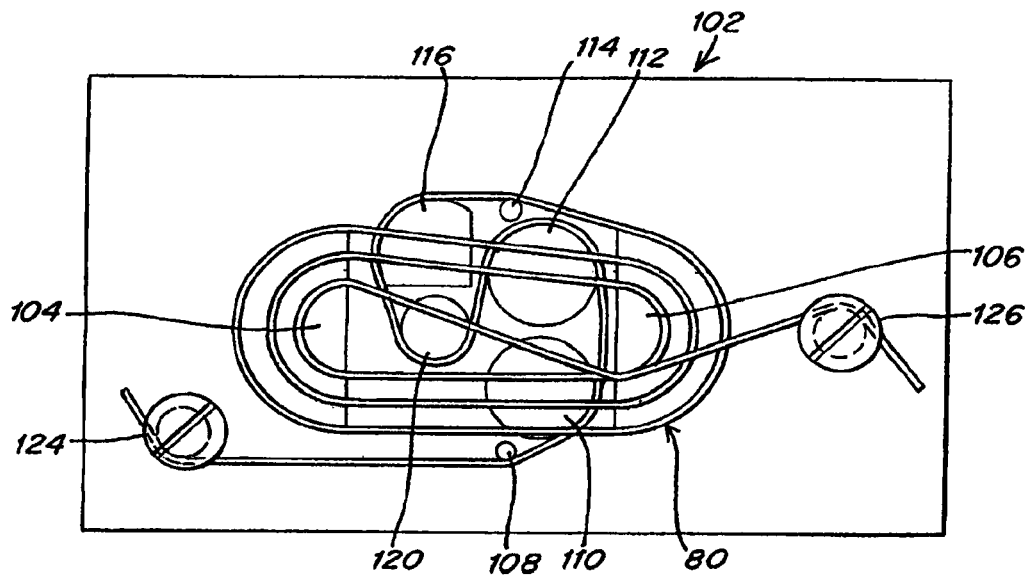
FIGS. 15A and 15B are a plan are a plan view and a side elevation view, respectively, of the jig of FIGS. 14A and 14B with the left atrial spiral section of the double spiral PFO closure clamp of FIG. 10 and with one half of the central connector of FIG. 13 formed thereon.
Figure 15B:
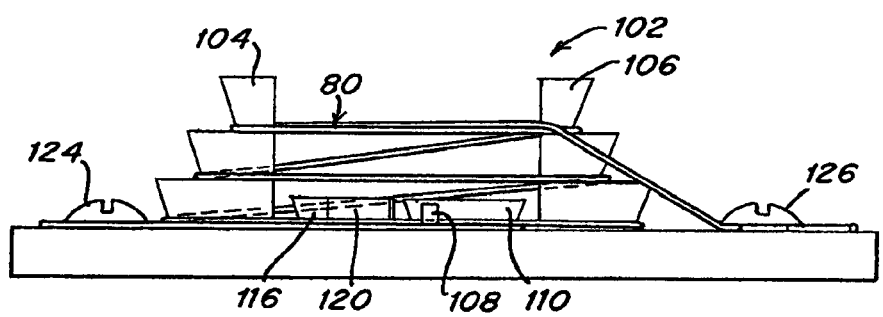

With reference to FIGS. 15A and 15B, the left atrial spiral section 80 and one half of the double "S" shaped connector 96 are formed by winding wire in a clockwise direction on the stepped sections 104 and 106. Beginning at the wire end retaining screw 124, the wire is passed around the pin 108 and across the round forms 110 and 112 and then around the form 112 and back to the round form 120. The wire is then brought around the round form 120 and then around the arcuate form 116 to the pin 114 to form one half of the double "S" shaped connector 96. From the pin 114, the wire is wound in a clockwise direction from the bottom to the top of the stepped sections 104 and 106 and is then secured to the wire end retaining screw 126. When the wire is thermal shape memory wire, it is annealed in place before the left atrial spiral section is removed from the jig 102.

Figure 16A:
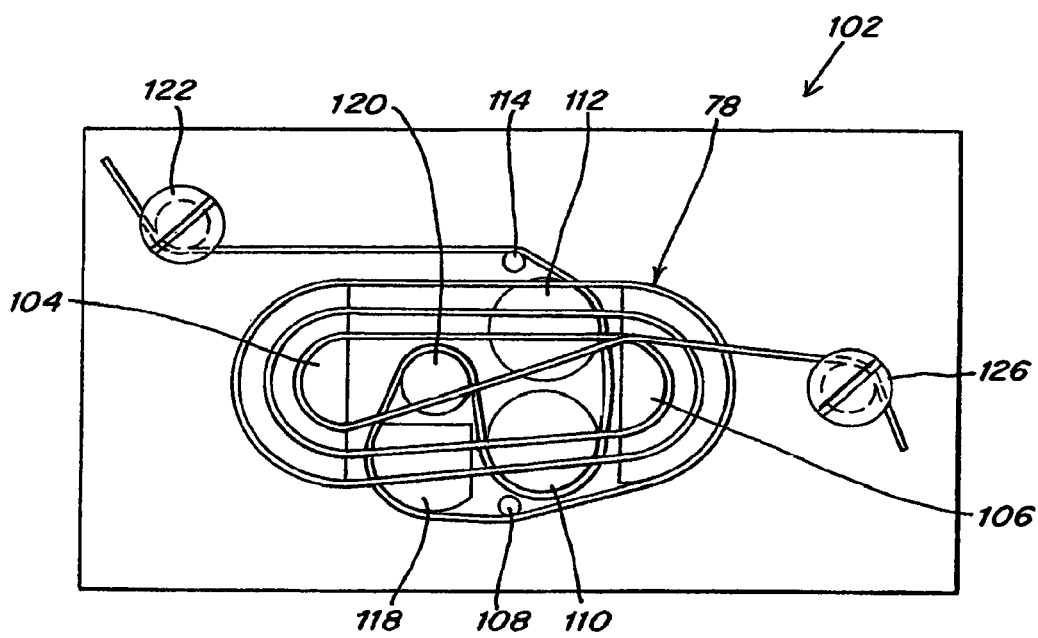
FIGS. 16A and 16B are a plan view and a view in side elevation, respectively, of the jig of FIGS. 14A and 14B with the right atrial spiral section of the double spiral PFO closure clamp of FIG. 10 and with one half of the central connector of FIG. 13 formed thereon.
Figure 16B:
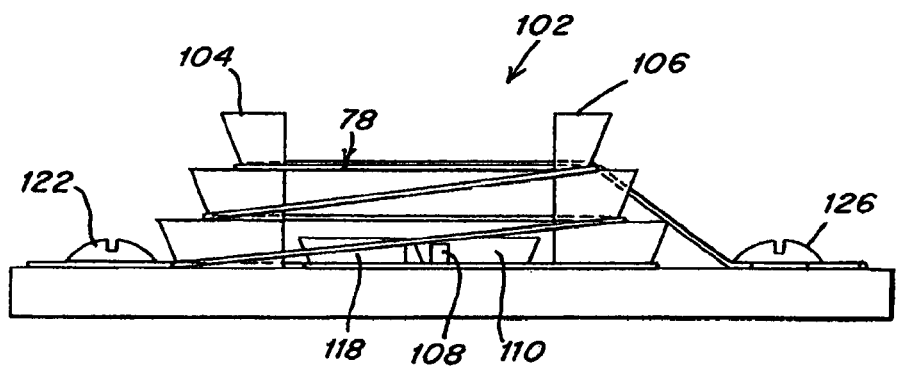

As shown in FIGS. 16A and 16B, the right atrial spiral section 78 is formed in the reverse manner and is wound counter clockwise on the stepped sections 104 and 106. Beginning at the wire end retaining screw 124, the wire is passed around the pin 114, the round forms 112 and 110, the round form 120 and an arcuate form 118 to the pin 108 to form the remaining half of the double "S" shaped connector 96. The wire is then wound in a counter clockwise direction from the bottom to the top of the stepped sections 104 and 106 and is then passed to the wire end retaining screw 126.

Figure 17A:
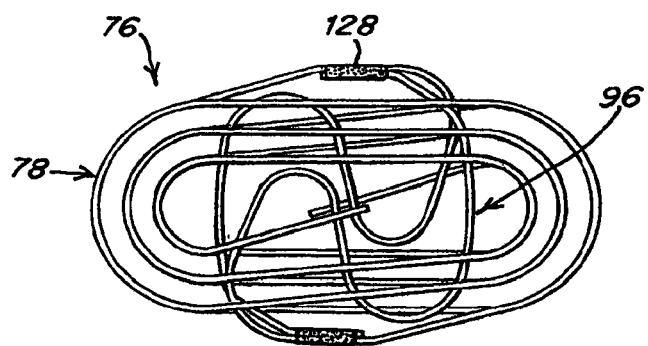
FIGS. 17A and 17B are a plan view and a side elevation view, respectively, of an expanded double spiral PFO closure clamp of FIG. 10 with one half of the central connector for FIG. 13.
Figure 17B:
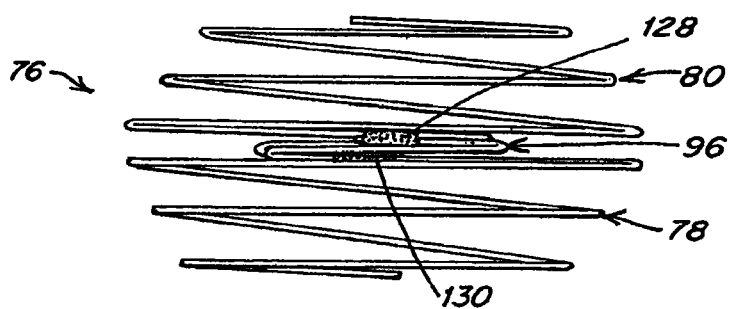

FIGS. 17A and 17B show the manner in which the two atrial spiral sections 78 and 80 are joined to form the double spiral PFO closure clamp 76. The two atrial spiral sections are oriented back to back to form the double "S" shaped connector 96, and are secured together at 128 and 130.

The double spiral PFO closure clamp 76 can be straightened with a tubular delivery device for delivery and may be delivered across the PFO by catheter using a pusher wire. The left atrial spiral section 80 is delivered first into the left atrium and flattened against the septum. The central double "S" shaped connector 96 is then unsheathed in the PFO channel, and finally the right atrial spiral section 78 is released against the septum in the right atrium.

Figure 18A:
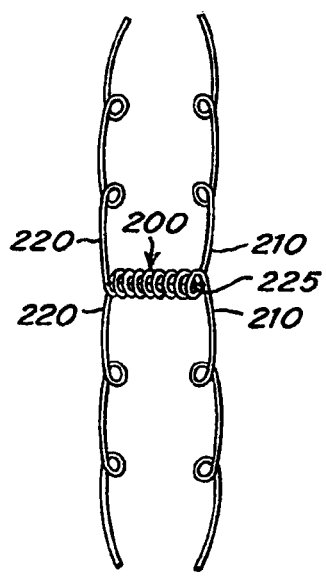
FIGS. 18A and 18B are alternative embodiments of a center joint of the present invention using helically wound wire.
Figure 18B:
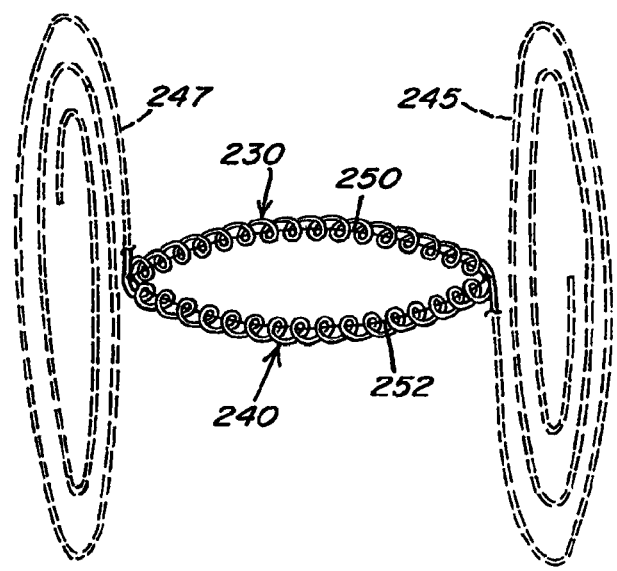

FIGS. 18A and 18B illustrate another embodiment of the center joint of the present invention. In this embodiment, the center joint is constructed of wire which has been wound to form a spiral 200 that connects ends 210 and 220. The spiral wound wire is flexible enough to accommodate a variety of anatomical configurations for the PFO tunnel. In this manner the spiral wound wire will conform to the PFO tunnel and will bend as necessary to allow the ends 210 and 220 to conform to the wall of the septum (not shown in this embodiment). The spirals US 1 DOCS 1788254V1 are illustrate in an exaggerated and open manner. Preferably the wire will be tightly close together and have a small overall diameter. Alternatively, the wire may have a thin wire strand 225 disposed in the helical wire to ensure that the spiral does not expand beyond the length of the wire strand. The wire 225 allows the center joint to be flexible and conform to the PFO tunnel without expanding beyond the longitudinal distance of the wire strand. The ends 210 and 220 are illustrated as the wire elements of the CardioSeal device more specifically described in U.S. Pat. No. 5,629,766 which is incorporated by reference into this specification.

FIG. 18B illustrates another embodiment of the center joint with a pair of helically wound wires 230, 240 that form the center joint. Ends 245, 247 of the device that contact the walls of the septum are illustrated as spirals. Of course, one skilled in the art would recognize the that the ends could be in a variety of configurations and dimensions, for example, spiral and CardioSeal configurations. The illustration exaggerates relative dimension of the center joint for clarity. In this embodiment, the center joint wires may also have wire strands 250, 252 disposed with the helically wound wire similar to the wire described in connection with FIG. 18A. In this embodiment, the strands 250, 252 may have a bent configuration, such as illustrated so that the center joint is disposed at the desired (e.g., centered) location.

Figure 19A:
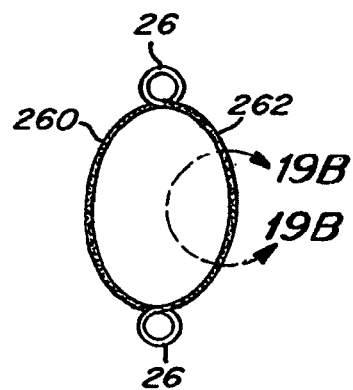
FIGS. 19A-19F are alternative embodiments of a center joint of the present invention using special surface preparations.
Figure 19B:
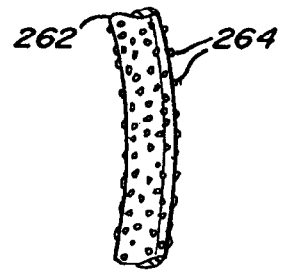

FIGS. 19A-19F illustrate various configuration of the center joint which may be used with a PFO closure device. In these illustrations, the center joint is illustrated without the ends. That is, only the portion that would be disposed within and next to the PFO tunnel is illustrated. The ends (not illustrated) would be connected at the locations identified by reference numberal 26. In these embodiments, different treatments are provided to the wires which assist in the positioning device and healing of the septum once the device is delivered. FIG. 19A illustrates two wires 260, 262 which are configured in an oval shape and are provided with a surface treatment which roughens the surface of the wires. FIG. 19B illustrates a magnified view of the wire 262 and shows bumps or roughness 264 on the wire. A variety of surface treatments may cause the roughness, for example, the wire may be electrocoated with a material that has a rougher surface. Alternatively, a mechanical knurling process may be used to roughen the surface. Finally, for example, the extrusion process of the wire manufacture may be modified to create a rough surface instead of a smooth. The rough surface may be randomly rough, as illustrated, or the rough surface may have a pattern, as would be typically achieved by a knurling or extrusion process. A rough surface in the center joint may provide certain advantages, for example, the rough surface may assure the center joint stays in place. Additionally, the roughened wires may stimulate a healing response by "irritating" the PFO tunnel in a manner that stimulates the body to heal and close the PFO tunnel.

Figure 19C:
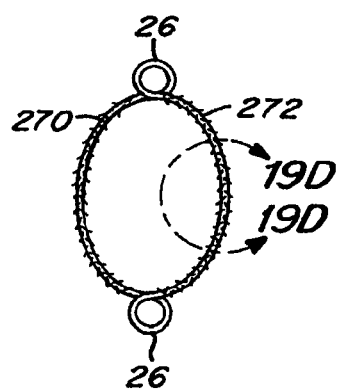
Figure 19D:
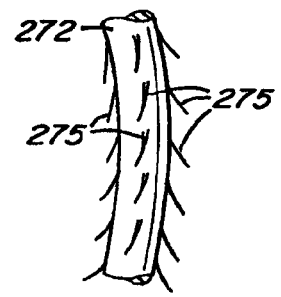

Other configurations for the wires of the center joint are possible. FIGS. 19C and 19D illustrate an alternative treatment of the wire. FIG. 19C shows the wires 270 and 272 which are adapted to be delivered into the PFO tunnel and the wires include a roughness that is different in one direction than the other. That is, if one were to run the wire between a thumb and an index finger in one direction, it would be relatively smooth and in the other direction, it would feel more rough. FIG. 19D illustrates the directional "quills" 275 which provide a smooth surface (downward as illustrated) and a rough surface (in the upward direction as illustrated). The direction of the quills may be configured to allow for convenient placement of the device within the PFO and for improved resistance to movement. The quills may be placed on the device in a variety of methods including a post extrusion process or directional knurling.

Figure 19E:
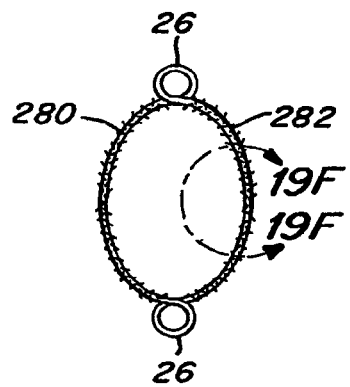
Figure 19F:
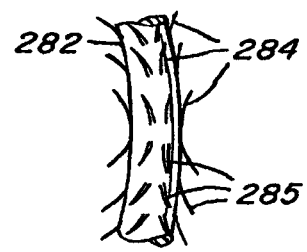

In another configuration, illustrated in FIGS. 19E and 19F, the quills are provided having opposed direction. In this embodiment, the wires 280 and 282 have quills 284 which are directed toward the center of the center joint. Similarly, the quills 285, on the other side of the center joint, are also directed toward the center of the center joint. This configuration may allow for improved stability within the PFO once delivered. In each of the embodiments, the healing response may be improved using roughened or quilled surfaces for the center joint.

Figure 20:
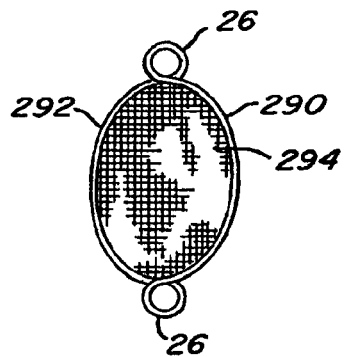
FIG. 20 is an alternative embodiment of a center joint of the present invention using a membrane.

FIG. 20 illustrates yet another configuration for the center joint that includes a fabric or mesh. The center joint is formed by wires 290 and 292, a mesh or fabric 294 is secured to the wires using a variety of known techniques. The mesh itself could be a biological material that stimulates a biological response. Alternatively, the mesh may be impregnated with a chemical or biological agent that may stimulate a biological healing response. Finally, the mesh could be the vehicle to deliver an agent to the PFO tunnel.

Figure 21A:
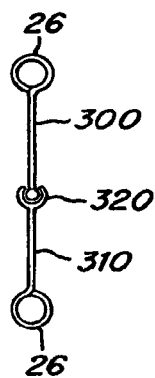
FIGS. 21A and 21B are alternative embodiments of a center joint of the present invention using a flexible joint.
Figure 21B:
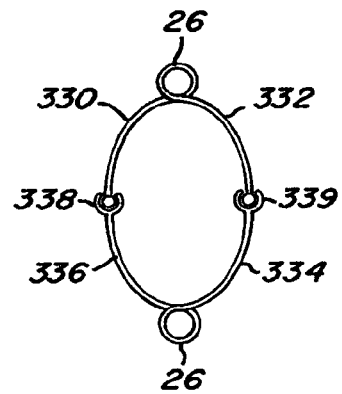

FIGS. 21A and 21B also illustrate alternative embodiments of the center joints which provide improved movement within the PFO tunnel for the center joint. Specifically, as illustrated in FIG. 21A, a "trailer hitch" design is used to improve the ability of the wires to conform within the PFO tunnel. Wires 300, 310 form a single wire center joint and are connected by a "trailer hitch" connection 320. The connection is configured to allow improved movement of the wires so that the ends (not illustrated) can conform to the septal walls without unnecessary stress. In a modification of the embodiment illustrated in FIG. 21A is shown in FIG. 21B. In the embodiment illustrated, the wires 330 and 332 are joined at end 26, which as in the other embodiments, will secure the end wire configuration that secures against septum. Similarly, the 334 and 336 are joined at the other side of the center joint. A pair of "trailer hitch" connections 338 and 340 are used to allow the movement of the wires in the center joint. The use of connection 338 and 340 may provide for sufficient flexibility to allow for thicker, more stable wires to be used as the center joint. The use of thicker, stiffer wires may allow for greater resistance from movement for the center joint.

Figure 22A:
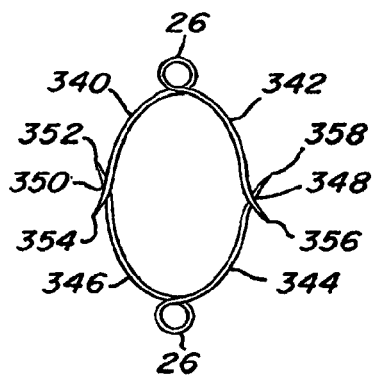
FIGS. 22A and 22B are alternative embodiments of a center joint of the present invention in which piercing wires are used to secure the device at the desired location.

In the embodiment of the invention illustrated in FIG. 22A the wires that form the oval connection provide a length of wire that could pierce into the septal tissue to secure the center joint in the desire location and, as a result, stabilize the PFO closure device. In the embodiment illustrated, wires 340 and 342 are joined to wires 344 and 346, respectively. The joints 348 and 350 may be welds or other joints that allow for the reduced profile that is desirable for delivery through a catheter. The ends 352, 354, 356 and 358 are designed to pierce the septum and allow for the improved stability described above.

Figure 22B:
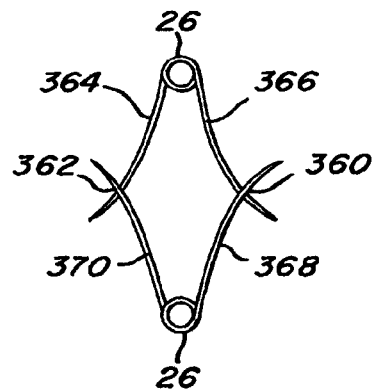

In a slightly modified configuration, the wires may be provided that are in a configuration illustrated in FIG. 22B. In this embodiment, joints 360 and 362 provide for the connection between the wires 364-370. The wires, as illustrated, have a shape that provides the greatest longitudinal width at the joint. This has the benefit of being able to keep the center joint centered within the PFO. In each of the embodiments described in connection with FIGS. 22A and 22B, the closure device is secured by the piercing elements. The wires can be constructed of a metal or a polymer, and have a circular cross-section or some other form such as a rectangle or polygon.

What is claimed is:

1. A device adapted to press together the septum primum and the septum secundum between the atrial chambers, the device comprising: two clamping members including elongate wire members that are spiral shaped, wherein the elongate members of the occluder terminate at one end of each in a ball, wherein one clamping member may be disposed on a side of the septum and a central connector which connects the two clamping members and passes through the tunnel wherein the central connector includes two wires that are spaced apart at a portion of their length so that the wires are proximate the lateral sides of the tunnel so that the device may be centered in a passage between the atrial chambers, wherein the central connector is connected to at least one clamping member at an inner part of the spiral shaped wire member.

2. The device of claim 1, wherein the central connector is connected to at least one clamping member at the outer part of the spiral shaped wire member.

3. The device of claim 1, wherein the force applied to the septum primum and septum secundum is created by the spiral shape of the elongate members.

4. The device of claim 3, wherein the clamping members are formed from nitinol.

5. The device of claim 1, wherein the central connector is formed from nitinol.

6. The device of claim 1, wherein the central connector is adapted to center the device in the lateral direction along a longitudinal passageway.

7. The device of claim 1, wherein the spiral shaped elongate members have a helical form.

8. The device of claim 1, wherein the connecting member comprises two elongate wires in a S shape.

9. The device of claim 1, wherein the connecting member comprises two elongate wires in a square shape.

* * * * *